United States Patent
Price

[19]

[11] Patent Number: 5,887,590
[45] Date of Patent: Mar. 30, 1999

[54] EYELID CLOSURE PATCH

[76] Inventor: John A. Price, 910 Craig Dr., Henderson, Ky. 42420

[21] Appl. No.: 908,822

[22] Filed: Aug. 8, 1997

[51] Int. Cl.$^6$ ....................................................... A61F 5/00
[52] U.S. Cl. ........................... 128/858; 604/294; 604/307; 602/54
[58] Field of Search ................................ 602/52, 54, 57, 602/74; 604/289, 294, 304, 307; 606/204.25; 607/141; 128/858

[56] References Cited

U.S. PATENT DOCUMENTS

| | | |
|---|---|---|
| 2,572,638 | 10/1951 | Loos . |
| 3,068,863 | 12/1962 | Bowman . |
| 3,092,103 | 6/1963 | Mower . |
| 4,134,401 | 1/1979 | Galician . |
| 4,331,136 | 5/1982 | Russell et al. . |
| 4,682,371 | 7/1987 | Helman . |
| 4,709,695 | 12/1987 | Kohn et al. . |
| 4,862,902 | 9/1989 | Goffman ................................... 128/858 |
| 4,867,146 | 9/1989 | Krupnick et al. ........................ 128/858 |
| 4,944,040 | 7/1990 | Riedel et al. ........................ 128/858 X |
| 4,951,658 | 8/1990 | Morgan et al. . |
| 4,995,114 | 2/1991 | Price, Jr. ............................. 128/858 X |
| 5,180,360 | 1/1993 | Rhame, Jr. ................................ 602/74 |
| 5,191,897 | 3/1993 | Meshel ................................ 128/858 X |
| 5,389,066 | 2/1995 | Rhame, Jr. ................................ 602/74 |
| 5,769,806 | 6/1998 | Radow ..................................... 602/41 |

Primary Examiner—Linda C. M. Dvorak
Attorney, Agent, or Firm—John Lezdey & Assoc.

[57] ABSTRACT

There is provided an eyelid closure patch for use by anesthesiologists to ensure that the patient's eyes are closed during surgery. The patch consists of a flexible transparent material which contains a layer of a transparent pressure sensitive water soluble gelatinous or hydrocolloidal adhesive. The patch has an adhesive free tab and a cover sheet.

14 Claims, 1 Drawing Sheet

EYELID CLOSURE PATCH

FIELD OF THE INVENTION

The present invention relates to a patch for placing over the eyelids of a patient during surgery. More particularly, there is provided an eye patch which is placed over the patient's eyes during surgery so as to prevent the drying of the eyes by the anesthesia.

BACKGROUND OF THE INVENTION

When patients are under anesthesia during surgery, the patient's eyes are generally taped shut by the use of ordinary tape. The taping of the eyes is performed for a variety of reasons. The most common reason is to protect them from abrasions or cornea drying out while under anesthesia. The patient does not tear while asleep so that the eye can dry out especially when under anesthesia. For the anesthesiologist, this requires tearing a strip of tape while wearing rubber gloves and gripping the tape to remove it after the operation. The use of ordinary tape provides a problem for the patient since the eyelashes can stick to the adhesive and cause problems.

U.S. Pat. Nos. 3,339,546 and 4,062,361, which are herein incorporated by reference, disclose hydrocolloids which can be used in the adhesives of the present invention.

U.S. Pat. No. 5,144,944 to Rice discloses a narrow skin closure dressing for eyelids comprising an adhesive layer on backing material, a multi-layered pad covering a portion of the face of the backing material and an outer layer of the backing material being free of adhesive. One or more side tabs are provided to assist in removal. The closure is primarily for use after surgical procedures.

The prior art closure dressings have the problems that they are difficult to handle with gloves. They are non-transparent and do not cover the eyes but only the upper eye lid so that the eyes can still be unprotected.

SUMMARY OF THE INVENTION

According to the invention, there is provided patches for maintaining a patient's eyes closed during surgery.

The patch of the invention comprises a flexible transparent backing material having a width to cover the upper and lower eyelids and a length substantially the length of the eye. The backing material is covered with a transparent pressure sensitive water soluble gelatinous or hydrocolloidal adhesive coating on one side except for a portion forming a tab which is adhesive free. A cover sheet is placed over the adhesive coating for handling and to maintain sterility. Advantageously, there is also a bottom cover sheet.

The patches can be provided in strips or in the form of a roll for easy handling.

It is therefore an object of the invention to provide an eye closure patches for use by anesthesiologists to maintain a patient's eyes closed during surgery.

It is a further object of the invention to provide an eye closure patch which can be easily removed after use.

It is still another object of the invention to provide an eye closure patch which can be readily available and easy to use by gloved anesthesiologists.

These and other objects and advantages will be more apparent when considered in view of the drawings and the description of the preferred embodiments.

DESCRIPTION OF THE PREFERRED EMBODIMENTS

Figure 1:
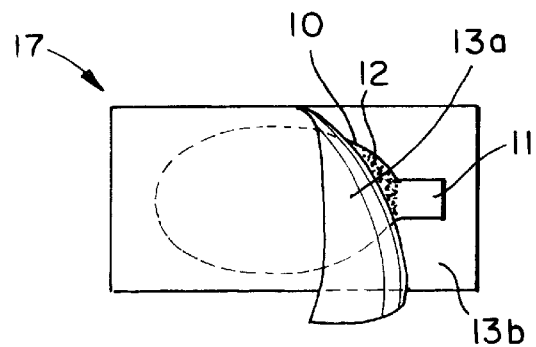
FIG. 1 is a sectional view of an eye patch of the present invention.
Figure 2:
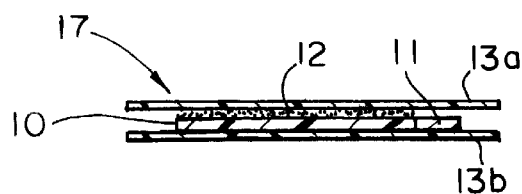
FIG. 2 is an elevational view of the patch of FIG. 1.

As illustrated in FIGS. 1 and 2, the patch 17 generally comprises a flexible transparent backing material 10 which is of a length and width to cover the eye and is coated with an adhesive coating 12. The adhesive coating 12 substantially covers the backing material 10 except for an adhesive free portion forming a tab 11 to assist in removal of the patch. A removable protective sheet 13a is placed over the adhesive coating 12 to protect the adhesive surface. Preferably, a lower sheet 13b is also used to encapsulate the patch 17 to keep it sterile.

When cover sheets 13a and 13b are utilized, they can be heat sealed together along the edges.

Figure 3:
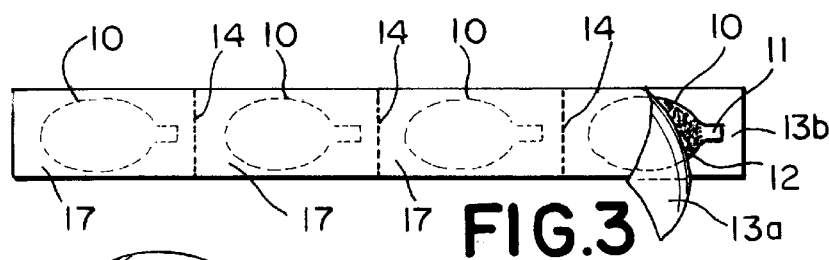
FIG. 3 is a top view of the patch of the invention in the form of a strip.

As illustrated in FIG. 3, the patches of the present invention can be supplied in the form of a strip 15 with each patch being separated at an area with perforations to form a tear strip.

Figure 4:
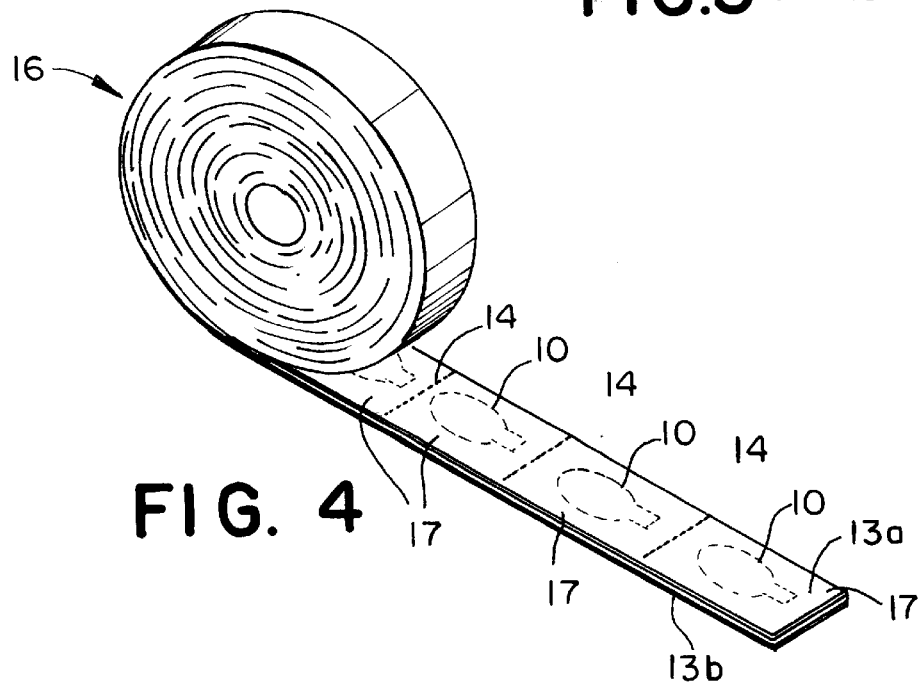
FIG. 4 is a perspective view of the eye patches of the invention in the form of a roll of tear strips.

For convenience in an operating room, the patches of the present invention can be supplied in one continuous roll 16 as illustrated in FIG. 4.

The backing material 10 can comprise any clear plastic material such as a polyolefin (polyethylene, polypropylene), polyvinyl alcohol, polyvinyl acetate, and the like.

The backing material 10 is preferably elliptically shaped having a width of about one inch and a length of about 1–2 inches. However, the patches can be formed of different sizes for use with children or adults.

The transparent material is necessary so that the anesthesiologist can observe the eyes of the patient.

The backing material 10 is provided with an adhesive free tab 11 for use in removing the patch from the eye. The tab 11 is generally about ¼ to ½ inch in length.

The adhesive which is utilized is a transparent pressure sensitive water soluble gelatinous or hydrocolloidal adhesive which can be easily removed without sticking to the eyelashes and can be used with comfort by the patient. A natural or synthetic hydrocolloid provides sufficient stickiness to cause the patch to adhere sufficiently during the operation. Suitable synthetic and natural water soluble hydrocolloids and gelatins include karaya gum, guara gum, collagen, polysaccharide gum, locust bean gum, powdered pectin, gelatin, carboxymethyl cellulose and the like.

If desired, the pressure sensitive adhesive can include 0 to 10% by weight of the usual modifiers, fillers, extenders, antioxidants, stabilizers and other such ingredients known in the art for inclusion in such compositions. Thus, for example, plasticizers or solvents such as mineral oil or petrolatum may be added to improve adhesive characteristics.

The extenders can include finely divided clays, bentonites, starches or other inert ingredients normally used in adhesive compositions. Antioxidants and stabilizers can be used at levels up to about 3% by weight of the total composition. Suitable oxidants and stabilizers include bitylzimate, 2,6-ditert-butyl-4 methyl phenol sold under the trademark IONOL by Shell Chemical Company, alkylated diphenyl phenols, non-allergenic substances such as zinc oxide can also be used as a stabilizer.

The adhesive preferably has a Williams plasticity number of about 1 to 4 mm according to the procedure of ASTM 0926-67 (1978).

The cover sheets or films can be prepared from polymeric films such as polyolefin polymers, vinylidene copolymers, fluorocarbon films, polyethylene terephthalate, acrylic polymers or the like.

The films or other substrates which may be employed in the invention may have a thickness of from 0.0005 to 0.05 inch. The adhesive is supplied to the backing material in sufficient amount to cause adherence.

As will be apparent to those skilled in the art, and as indicated above, many modifications and variations of the foregoing detailed description are possible within the spirit and scope of the present invention.

What is claimed is:

1. A patch for maintaining a patient's eye closed during surgery which comprises a flexible transparent backing material having a width to cover the upper and lower eyelids and a length substantially the length of the eye, at least one non-adhesive tab portion on an end of said backing material, a transparent pressure sensitive water soluble gelatinous or hydrocolloidal adhesive coating on one side of said backing material, and a cover sheet over said adhesive coating.

2. The patch of claim 1 wherein said backing material comprises a plastic.

3. The patch of claim 2 wherein said plastic is selected from the group consisting of polypropylene, polyethylene, an acrylic polymer and polyvinyl alcohol.

4. The patch of claim 1 wherein said adhesive comprises a hydrogel.

5. The patch of claim 1 wherein said adhesive comprises a natural gum.

6. The patch of claim 5 wherein said gum is karaya gum.

7. The patch of claim 5 wherein said gum is guara gum.

8. The patch of claim 5 wherein said adhesive comprises a polysaccharide gum.

9. The patch of claim 1 wherein said adhesive includes a stabilizer.

10. The patch of claim 9 wherein said stabilizer is non-allergenic.

11. The patch of claim 10 wherein said stabilizer is zinc oxide.

12. The patch of claim 1 further containing a bottom cover.

13. The patch of claim 1 comprising a multiplicity of strips.

14. The patch of claim 1 in the form of a roll of tear strips.

* * * * *